United States Patent
Daniels et al.

[11] Patent Number: 5,295,274
[45] Date of Patent: Mar. 22, 1994

[54] LIQUID DISPENSING APPARATUS

[76] Inventors: Rickey A. Daniels, 2621 Dinah; Thomas R. Daniels, 11413 Oak Tree, both of Balch Springs, Tex. 75180

[21] Appl. No.: 838,534

[22] Filed: Feb. 19, 1992

[51] Int. Cl.$^5$ .............................................. A47K 3/22
[52] U.S. Cl. .......................................... 4/443; 4/448; 604/30; 604/257; 604/279
[58] Field of Search ............ 4/420.1, 420.2, 420.3, 4/420.4, 420.5, 443, 448; 222/155, 159; 604/259, 279, 257, 30

[56] References Cited

U.S. PATENT DOCUMENTS

| | | | |
|---|---|---|---|
| 1,732,528 | 10/1929 | O'Rourke, Jr. et al. | 604/259 |
| 2,968,303 | 1/1961 | Tenscher | 604/259 |
| 3,662,407 | 5/1972 | Colucci | 4/420.2 |
| 3,847,150 | 11/1974 | Scheuermann . | |
| 3,914,804 | 10/1975 | Schrader et al. | 4/420.2 X |
| 3,921,635 | 11/1975 | Gauthier . | |
| 4,000,742 | 1/1977 | DiGiacomo . | |
| 4,406,025 | 9/1983 | Huck et al. | 4/443 |
| 4,950,231 | 8/1990 | Liu | 604/39 |
| 5,090,067 | 2/1992 | Cogdill | 4/420.2 |

FOREIGN PATENT DOCUMENTS

| | | | |
|---|---|---|---|
| 1163343 | 9/1958 | France . | |
| 633896 | 2/1962 | Italy . | |
| 9113220 | 9/1991 | World Int. Prop. O. | 4/448 |

*Primary Examiner*—William A. Cuchlinski, Jr.
*Assistant Examiner*—W. Morris Worth
*Attorney, Agent, or Firm*—Daniel V. Thompson

[57] ABSTRACT

Liquid dispensing apparatus includes a tank for storing liquid to be dispensed, a fill line communicating with an interior of the tank and adapted to be coupled to a source of the liquid, a heating element for heating the liquid, a heating control device for controlling the heating element to heat the liquid to a predetermined temperature, a dispensing device for dispensing liquid from the tank under pressure and a dispensing control device for selectively controlling the dispensing of the liquid by the dispensing device. The fill line is adapted to be connected to existing plumbing, such as a toilet water supply line behind a wall adjacent the toilet. The tank is adapted to be housed in a recessed wall cabinet adjacent the toilet so that the entire apparatus is hidden from view when not in use. The tank includes a sump portion defining a lowermost portion of the tank, to facilitate complete evacuation of liquid from the tank. An electrically operable pump is preferably located at the bottom of the sump portion for discharging liquid therefrom. A sight gauge is located on the front of the tank to permit visual observation of the level of liquid in the tank. User-operable switches are provided to allow a user to manually control the pump and the heating element. A thermostat is provided for automatic control of the heating element.

5 Claims, 2 Drawing Sheets

LIQUID DISPENSING APPARATUS

FIELD OF INVENTION

This invention relates generally to liquid dispensing apparatus and in particular to a liquid dispensing apparatus for hygienic use.

BACKGROUND OF THE INVENTION

Liquid dispensing apparatus for hygienic use have included bags for holding the liquid and a liquid dispensing nozzle attached to the bag by means of a flexible hose or the like. The bag is typically hung at an elevated position above the nozzle, such that liquid flows by gravity from the bag through the flexible hose and into the nozzle, from which it is dispensed. An obvious disadvantage of this type of device is that the discharge velocity is usually insufficient for hygienic use.

Other prior art devices include douche and other hygienic devices adapted for attachment to a water source, such as a bathroom faucet, shower head or the like. Devices of this type are disclosed in U.S. Pat. Nos. 3,847,150, 3,921,635 and 4,000,742, French Patent 1,163,343 and Italian Patent 633,896. One disadvantage of this type of device is that the device must be attached to the water source each time the device is used or alternatively, if the device is permanently attached to the water source, it is usually unsightly and detracts from the appearance of the bathroom in which the device is installed. Furthermore, it is difficult to control the pressure and temperature of the liquid discharged from this type of device.

DISCLOSURE OF THE INVENTION

In accordance with the present invention, a liquid dispensing apparatus is provided having a tank for storing the liquid to be dispensed, a liquid fill line communicating with an interior of the tank and adapted to be coupled to a source of the liquid for introducing liquid into the tank, heating means for heating the liquid in the tank, heating control means for controlling the heating means to heat the liquid to a predetermined temperature, dispensing means for dispensing liquid from the tank under pressure and dispensing control means for selectively controlling dispensing of the liquid.

In accordance with one feature of the invention the tank includes a sump portion, which is lower than the remainder of the tank. A pump is located in the sump portion for discharging liquid therefrom. The pump is preferably located at the lowest point of the sump to facilitate the complete removal of liquid from the tank.

In accordance with another feature of the invention, the dispensing means includes a flexible hose in fluid communication with the pump and a nozzle located at a distal end of the hose for dispensing the liquid. The dispensing control means includes a user operable valve for controlling the flow of liquid through the nozzle.

In accordance with yet another feature of the invention, the tank includes a sight gauge, which allows a user to visually monitor the level of liquid in the tank. A user-operable fill valve is provided for allowing the user to regulate the volume of liquid entering the tank through the fill line.

The tank is adapted to fit in a cabinet or other recess behind a structural wall, such that the tank is not visible from within the living space adjacent the wall when the tank is not in use. The fill line is adapted to be coupled to a water supply line which supplies water to a bathroom toilet tank. The connection between the fill line and the water supply line is preferably made behind the structural wall adjacent the toilet so that the fill line is not visible from inside the bathroom in which the toilet is located. The front panel of the liquid storage tank is removable to facilitate cleaning the interior thereof. The tank also hall a top opening for introducing material into the tank. For example, vinegar or other hygienic liquids can be introduced through the top opening. The top opening is normally covered with a screw on/screw off cap.

DETAILED DESCRIPTION OF THE PREFERRED EMBODIMENT

Figure 1:
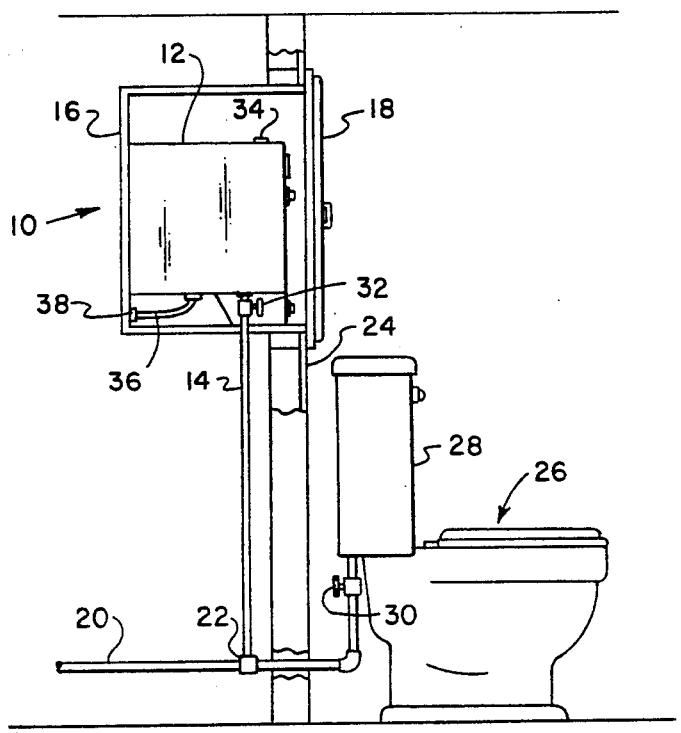
FIG. 1 is a side elevation view of a liquid dispensing apparatus, according to the present invention, housed in a recessed cabinet.

In the description which follows, like parts are marked throughout the specification and drawings with the same respective reference numerals. The drawings are not necessarily to scale and in some instances proportions may have been exaggerated in order to more clearly depict certain features of the invention.

Referring now to FIG. 1, an apparatus 10 for dispensing liquid includes a tank 12 for storing the liquid to be dispensed, a liquid fill line 14 in fluid communication with a bottom part of tank 12 for introducing liquid into tank 12. Tank 12 is preferably housed in a recessed wall cabinet 16. Cabinet 16 includes a hinged door 18, which renders apparatus 10 substantially invisible when door 18 is in a closed position, as shown. Access to apparatus 10 is permitted when door 18 is in an open position. Tank 12 and cabinet 16 are preferably small enough to fit in the space between wall studs (e.g., approximately 16 inches wide and approximately 3½ inches depth of recess behind a wall 24).

Fill line 14 is adapted to be coupled to a water supply line 20, as indicated at 22, behind wall 24 adjacent a bathroom commode 26. Water supply line 20 is a typical plumbing conduit used to supply water to a tank 28 of commode 26. A manually operable shut-off valve 30 is located beneath commode tank 28 for selectively shutting off the flow of water to commode tank 28.

A fill valve 32 is located inside cabinet 16 for controlling the flow of water through fill line 14 into tank 12. A screw on/screw off cap 34 is located on top of tank 12 to cover a top opening (not shown) in tank 12 through which hygienic liquid, such as vinegar, can be introduced into tank 12. Alternatively, tank 12 can be configured to be portable, with the water also being introduced into tank 12 through the top opening.

An electrical conduit 36 has a multi-pronged plug 38 at one end thereof for connecting the electrical components of apparatus 10 to a source of electrical power, such as an electrical socket (not shown) mounted within cabinet 16. The electrical components of apparatus 10 will be described in greater detail hereinafter.

Other than electrical conduit 36, apparatus 10 is not visible when cabinet door 18 is closed, so that apparatus 10 does not detract from the appearance of the adjacent bathroom in which commode 26 is located. Furthermore, housing apparatus 10 in recessed wall cabinet 16 conserves valuable space within the adjacent bathroom.

Figure 2:
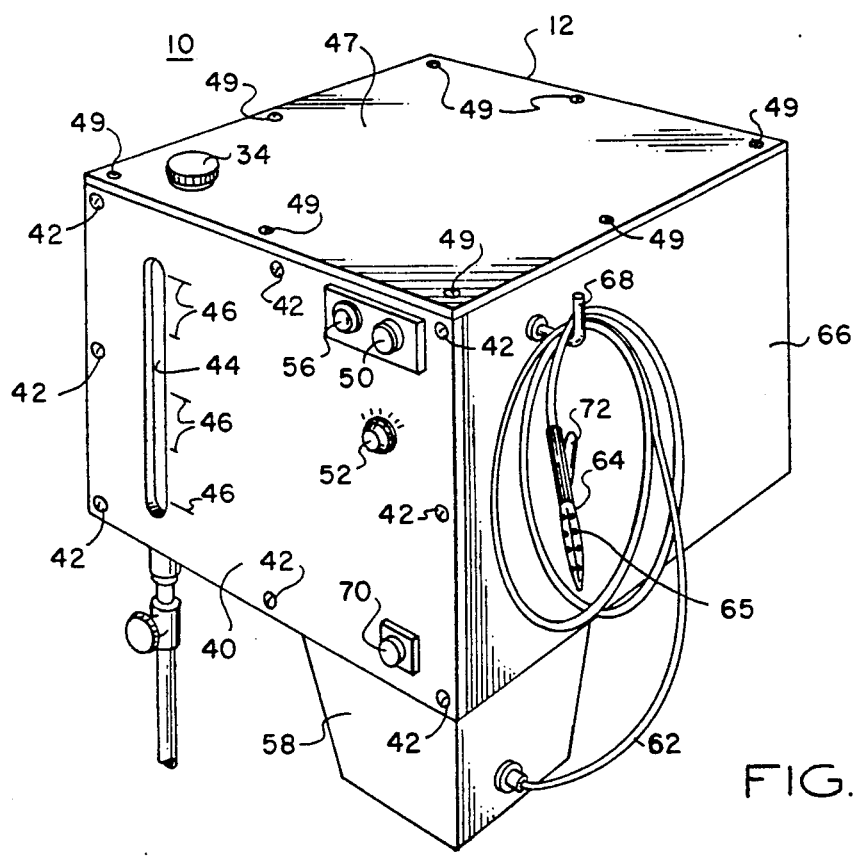
FIG. 2 is a perspective view of the liquid dispensing apparatus of FIG. 1.
Figure 3:
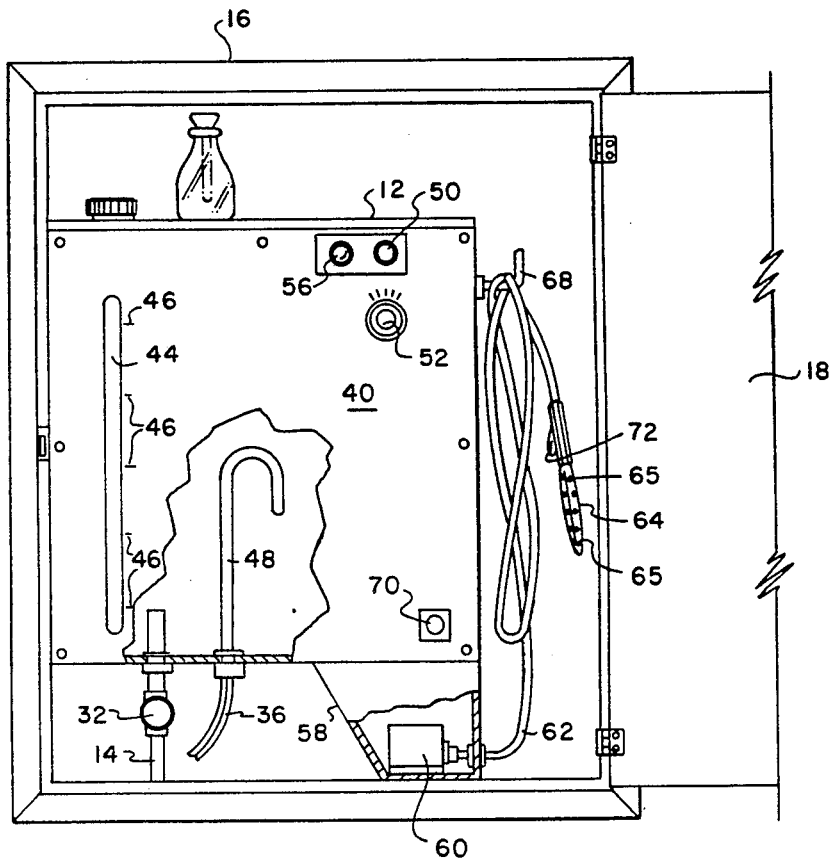
FIG. 3 is a front elevation, partial cutaway view of the liquid dispensing apparatus of FIG. 1.

Referring now to FIGS. 2 and 3, tank 12 is substantially box-shaped and includes a front panel 40, which is removably attached to the remainder of tank 12 by a plurality of attachment screws 42. Front panel 40 is removable to facilitate cleaning the inside of tank 12. A sight gauge 44 is located on front panel 40, to permit the user to visually monitor the level of liquid within tank 12. Sight gauge 44 is preferably a transparent glass tube with vertically spaced indicia 46, to indicate the volume of liquid corresponding to the various levels indicated by indicia 46. Top panel 47 is also removably attached to the remainder of tank 12 by attachment screws 49.

As shown in FIG. 3, an electrical heating element 48 is located inside tank 12 for heating the liquid stored therein. Heating element 48 is activated by means of a user-operable switch 50 located on front panel 40 (FIG. 2). A thermostat 52 is also located on front panel 40 for controlling the temperature of liquid inside tank 12. Thermostat 52 includes a temperature gauge, which allows the user to set thermostat 52 to a desired temperature. A temperature sensor (not shown) is electrically coupled to thermostat 52 for sensing the temperature of the liquid inside tank 12. When the temperature reaches the desired temperature, the thermostat switch is open, thereby deactivating heating element 48. When heating element 48 is deactivated, indicator light 56 is illuminated, indicating that the liquid temperature has reached the desired temperature.

Tank 12 includes a sump portion 58, which defines the lowermost portion of tank 12. Sump portion 58 has sloped sides to facilitate drainage of liquid into the lowermost portion of tank 12. Sump portion 58 is preferably removably attached by attachment screws (not shown) or the like to allow sump portion 58 to be removed for cleaning. An electrically operable liquid pump 60 is located at the bottom of sump portion 58 for discharging liquid from tank 12 through a flexible hose 62, which is connected to the pump discharge. A nozzle 64, such as a conventional douche nozzle having an elongated tip with a plurality of orifices 65 spaced along the tip, is attached at a distal end of hose 62 for dispensing liquid under pressure through orifices 65. A side panel 66 of tank 12 has a hook 68 projecting therefrom for supporting hose 62 in a coiled position, as can be best seen in FIG. 2.

A user-operable switch 70 is located on front panel 40 for selectively starting and stopping pump 60. Pump 6 0 is preferably operated until all of the liquid has been evacuated from tank 12. Pump 60 preferably includes an automatic cut-off switch for disabling pump 60 when suction is lost. Pump 60 can also be stopped by pushing pump switch 70 when pump 60 is in operation.

Nozzle 64 further includes a cut-off valve (not shown), which is operable by means of a spring-biased lever 72. Lever 72 is normally biased to a closed valve position for shutting off the flow of liquid through nozzle 64. When lever 72 is squeezed by the user, the cut-off valve is opened, thereby allowing liquid to flow into nozzle 64 for being dispensed through orifices 65.

Figure 4:
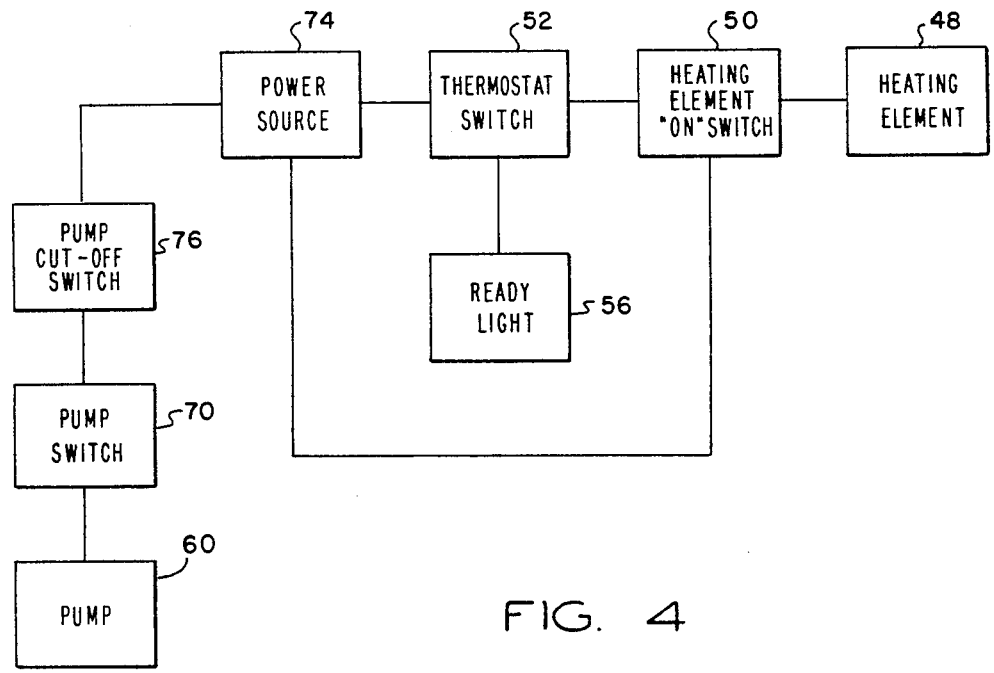
FIG. 4 is a schematic diagram of the electrical components of the liquid dispensing apparatus of FIG. 1.

In operation, when one desires to use apparatus 10, the user opens fill valve 32, to allow water to flow under pressure from water supply line 20 through fill line 14 into tank 12. The user can visually monitor the level of liquid in tank 12 through sight gauge 44, so that the flow of water can be shut off when the level has reached the desired level. The maximum capacity of tank 12 is preferably one-half gallon. The user should not introduce any more water into tank 12 than is needed for immediate use. Referring also to FIG. 4, the user then connects electrical conduit 36 to a power source 74, such as a wall-mounted electrical outlet, sets thermostat 52 to a desired temperature of the liquid and pushes heating switch 50 to activate heating element 48. When the temperature of the liquid has reached the desired temperature, the thermostat switch shuts off power to heating element 48, thereby disabling element 48. When element 48 is disabled, ready light 56 is illuminated, thereby providing a visual indication that the liquid has been heated to the desired temperature.

When the liquid in tank 12 is at the desired temperature, the user pushes pump switch 70, to activate pump 60. The user then removes hose 62 and nozzle 64 from hook 68 and positions nozzle 64 in the desired position for dispensing the liquid. The user controls the flow of liquid through nozzle 64 by selectively squeezing and releasing lever 72. The liquid should be dispensed through nozzle 64 until all of the liquid has been discharged from tank 12. When pump 60 loses suction, indicating, that substantially all of the water has been evacuated from sump portion 58, pump cut-off switch 76 automatically disables pump 60. Pump 60 can be manually disabled by pushing pump switch 70 when pump 60 is in operation. If it is desired to add hygienic products to the liquid, cap 34 is removed and the hygienic product is introduced into tank 12 through the top opening therein.

The liquid dispensing apparatus according to the present invention allows the user to precisely control the temperature of the dispensed liquid and the velocity at which the liquid is dispensed. The user can also control the volume of liquid dispensed by regulating the amount of liquid introduced into the tank before each use. Hygienic products can be added to the liquid through the top opening in the tank. The removable front panel facilitates cleaning of the interior of the tank.

The entire apparatus can be housed in a recessed wall cabinet so that the apparatus can be hidden from view when not in use. The apparatus is adapted to be connected to existing plumbing, such as a toilet water supply line, the connection being preferably behind the wall adjacent the toilet. Housing the apparatus in a recessed wall cabinet also has the advantage of conserving valuable space within the adjacent bathroom.

Various embodiments of the invention have now been described in detail. Since it is obvious that many changes in and. additions to the above-described preferred embodiment may be made without departing from the nature, spirit and scope of the invention, the invention is not to be limited to said details, except as set forth in the appended claims.

What is claimed is:

1. Apparatus for dispensing liquid, comprising:
   a tank for storing liquid;
   liquid fill means communicating with an interior of said tank for allowing liquid to be introduced into the tank;
   heating means for heating the liquid in said tank heating control means for controlling said heating means to heat the liquid to a predetermined temperature;

dispensing means for dispensing liquid from said tank under pressure;

dispensing control means for selectively controlling the dispensing of the liquid by said dispensing means;

wherein said dispensing means includes an electrically-operable pump, said apparatus further including user-operable switch means for controlling the operation of said pump; and wherein said tank includes a sump portion defining a lowermost portion of said tank, said pump being located in said sump portion, said pump having electrical cut-off means for automatically disabling said pump when liquid has been substantially evacuated from said sump portion by said pump.

2. Apparatus for dispensing liquid, comprising:

a tank for storing liquid to be dispensed, said tank having a sump portion defining a lowermost portion of said tank;

a liquid fill line communicating with an interior of said tank and adapted to be connected to a source of the liquid;

first user operable valve means for controlling the flow of liquid through said fill line into said tank;

sight gauge means located on said tank to allow visual monitoring of the level of liquid in said tank;

an electrically-operable heating element located in said tank for heating the liquid stored therein;

thermostat means controllable by the user for controlling said heating element to heat the liquid stored in said tank to a user-selected predetermined temperature;

first manually operable switch means for controlling the operation of said heating element;

illumination means for providing a visual indication when the temperature of the liquid in said tank corresponds to the user-selected predetermined temperature;

electrically-operable pump means located in said sump portion for discharging liquid from said sump portion;

second manually operable switch means for controlling the operation of said pump means;

a flexible conduit connectable to a discharge side of said pump means for conducting the liquid discharged by said pump means;

nozzle means located on a distal end of said flexible conduit; and second manually operable valve means for controlling the flow of liquid through said nozzle means.

3. The apparatus of claim 2 wherein said tank has a top opening through which material can be introduced into said tank, said apparatus further including a cap positionable to cover said top opening.

4. The apparatus of claim 3 wherein said pump includes power-cut off means for automatically disabling said pump means when the liquid has been substantially evacuated from said sump portion.

5. The apparatus of claim 4 wherein said nozzle means is an elongated nozzle having a plurality of orifices spaced along said nozzle.

* * * * *